(12) United States Patent
Deckert et al.

(10) Patent No.: US 11,097,125 B2
(45) Date of Patent: Aug. 24, 2021

(54) MICRO-ELECTRODE ARRAY AND METHOD FOR PRODUCING A MICRO-ELECTRODE ARRAY

(71) Applicants: Leibniz-Institut fuer Neurobiologie Magdeburg, Magdeburg (DE); Otto-Von-Guericke Universitaet Magdeburg, Madgeburg (DE)

(72) Inventors: Martin Deckert, Magdeburg (DE); Michael Lippert, Magdeburg (DE); Bertram Schmidt, Villingen-Schwenningen (DE); Frank Ohl, Osterweddingen (DE); Armin Dadgar, Berlin (DE)

(73) Assignees: LEIBNIZ-INSTITUT FUER NEUROBIOLOGIE MAGDEBURG, Magdeburg (DE); OTTO-VON-GUERICKE UNIVERSITAT MAGDEBURG, Magdeburg (DE)

( * ) Notice: Subject to any disclaimer, the term of this patent is extended or adjusted under 35 U.S.C. 154(b) by 248 days.

(21) Appl. No.: 16/082,150

(22) PCT Filed: Mar. 13, 2017

(86) PCT No.: PCT/EP2017/055816
§ 371 (c)(1),
(2) Date: Sep. 4, 2018

(87) PCT Pub. No.: WO2017/157839
PCT Pub. Date: Sep. 21, 2017

(65) Prior Publication Data
US 2019/0091483 A1    Mar. 28, 2019

(30) Foreign Application Priority Data

Mar. 15, 2016 (DE) .................. 10 2016 104 750.3

(51) Int. Cl.
*A61N 5/06* (2006.01)
*A61B 5/00* (2006.01)
(Continued)

(52) U.S. Cl.
CPC .......... *A61N 5/0622* (2013.01); *A61B 5/0084* (2013.01); *A61B 5/24* (2021.01);
(Continued)

(58) Field of Classification Search
CPC .. A61B 5/0084; A61B 5/04001; A61B 5/0478
See application file for complete search history.

(56) References Cited

U.S. PATENT DOCUMENTS

2012/0018901 A1    1/2012  Variot et al.
2014/0350375 A1   11/2014  Wolfe et al.

FOREIGN PATENT DOCUMENTS

DE       692 15 991 T2    5/1997
DE   10 2012 002 663 A1   8/2013
(Continued)

OTHER PUBLICATIONS

Kim et al.; "3D silicon neural probe with integrated optical fibers for optogenetic modulation"; Lab on a Chip, vol. 15, No. 14, Jul. 21, 2015, pp. 2939-2949.

*Primary Examiner* — Joseph M Dietrich
(74) *Attorney, Agent, or Firm* — W&C IP

(57) ABSTRACT

A micro-electrode array (1) comprising a flexible substrate (2) and a multiplicity of electrodes (3) for electrically measuring neural activity is described. The electrodes (3) are arranged on the substrate (2), project from the plane of the substrate (2) and have a core (4). A plurality of measurement lines (9) that are electrically insulated from one another are arranged around the core (4). Adjacent to the end surface (7) of the core (4), at the end of the electrodes (3) there are a plurality of electrode surfaces (8) arranged in a manner (Continued)

Figure 1:
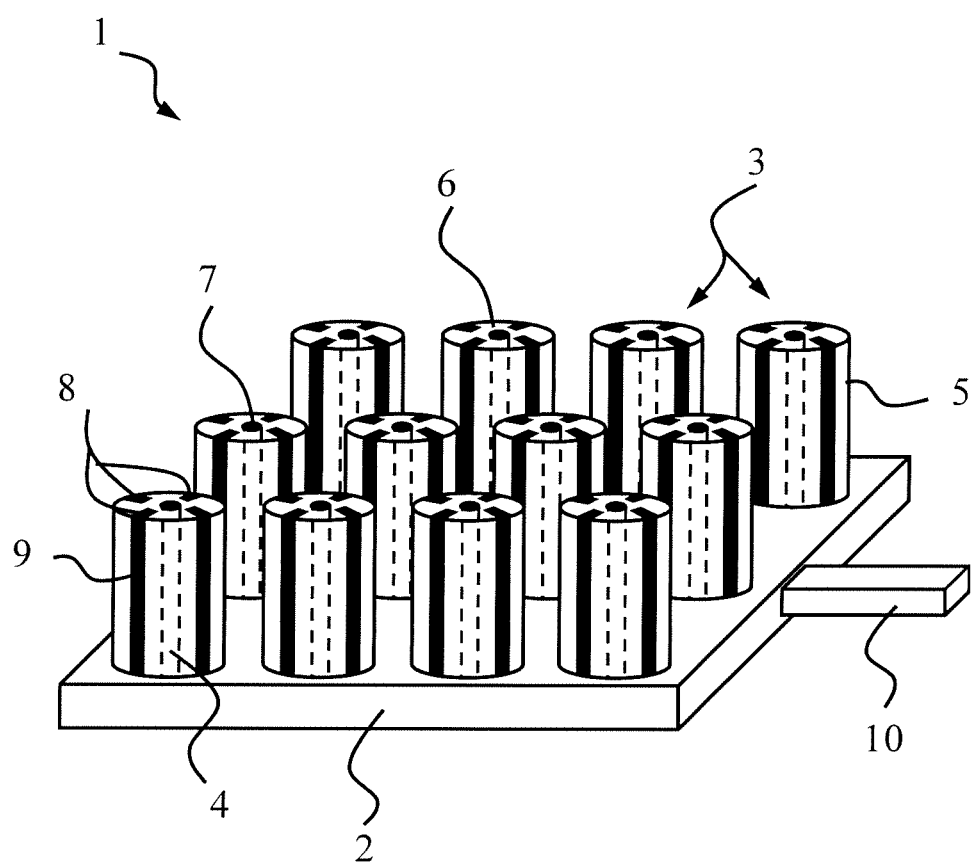

distributed spatially around the end surface (7), said electrode surfaces in each case being electrically conductively connected to an associated measurement line (9). The microelectrode array (1) is passivated with a polymer-containing material, such as e.g. polyimide, such that only the electrodes (3) electrically contact neural tissue with their electrode surfaces (8, E1, E2).

14 Claims, 3 Drawing Sheets

(51) Int. Cl.
*A61B 5/24* (2021.01)
*A61B 5/291* (2021.01)
*B29D 11/00* (2006.01)
*A61N 5/067* (2006.01)
*B29K 33/00* (2006.01)

(52) U.S. Cl.
CPC ........ *A61B 5/291* (2021.01); *B29D 11/00663* (2013.01); *A61B 2562/028* (2013.01); *A61B 2562/0209* (2013.01); *A61B 2562/046* (2013.01); *A61B 2562/125* (2013.01); *A61B 2562/164* (2013.01); *A61N 2005/067* (2013.01); *A61N 2005/0626* (2013.01); *A61N 2005/0651* (2013.01); *A61N 2005/0666* (2013.01); *B29K 2033/12* (2013.01)

(56) References Cited

FOREIGN PATENT DOCUMENTS

| | | |
|---|---|---|
| WO | 2014067963 A1 | 5/2014 |
| WO | 2015/038974 A1 | 3/2015 |
| WO | 2015143443 A1 | 9/2015 |

MICRO-ELECTRODE ARRAY AND METHOD FOR PRODUCING A MICRO-ELECTRODE ARRAY

The invention relates to a micro-electrode array comprising a flexible substrate and a multiplicity of electrodes for electrically measuring neural activity and for optical stimulation, wherein the electrodes are arranged on the substrate, project from the plane of the substrate and have a core.

The invention furthermore relates to a method for producing such a micro-electrode array.

Micro-electrodes are used in order to be able to measure e.g. neural activities in the brain robustly and simply. In order to measure not just the neural activity in each case of a few cells, electrodes are arranged in arrays or matrices that can comprise up to a few thousand individual electrodes. The high number of channels thus enables simultaneous derivation from so many neurons that the data can be used for realizing e.g. brain-computer interfaces (Brain Machine Inferfaces, BMI). Not only neural coding patterns can be analyzed by this means. Such micro-electrode arrays can also be used to facilitate communication between patients and the outside world or to enable an interaction for patients.

US 2013/0046148 A1 discloses an electrode array comprising conically tapering, acicular electrodes having an optical waveguide formed from a central shaft. The outer sides of the conical, tapering electrodes are coated in electrically conductive fashion fully circumferentially in order to measure a neural activity with each electrode tip.

A similar embodiment of a micro-electrode array comprising an optically conductive core which is surrounded with a metal layer fully circumferentially for light guiding and electrical outgoing conduction is described in J. Zhang, F. Laiwalla, J. A. Kim, H. Urabe, R. Van Wagenen, Y.-K. Song, B. B. Connors, F. Zhang, K. Deisseroth, A. V. Nurmikko: "Integrated device for optical stimulation and spatiotemporal electrical recording of neural activity in light-sensitized brain tissue", in: J Neural Eng. 2009 October; 6(5).

DE 10 2012 110 358 A1 describes a micro-electrode array comprising a multiplicity of electrodes provided in the form of one or more metallization planes in a substrate. Moreover, electrical light sources of an optical stimulation unit are accommodated in the substrate or arranged at the surface of the substrate in a manner distributed over the areal extent of the substrate.

S. Chen, W. Pei, Q. Gui, Y. Chen, S. Zhao, H. Wang, H. Chen: "A fiber-based implantable mulit-optrode array with contiguous optical and electrical sites", in: J. Neural Eng. 10 (2013) describe an electrode arrangement comprising a plurality of rod-shaped electrodes which taper at the end and which have a light guiding core and a layer surrounding the core. An electrode surface is arranged circumferentially at the tip, said electrode surface being led by way of an electrically conductive layer around the lateral surface of the pin electrode to a connection point at a connector. The pin electrodes are inserted into the insulating material housing of the connector and electrically conductively contacted there.

When the electrodes are employed, the tissue in the vicinity of the electrode tips is damaged, thus resulting in a decline in the neural activity in the direct vicinity of the electrode tips. Moreover, the assembly of the micro-electrode arrays is expensive and difficult.

Taking this as a departure point, it is an object of the present invention to provide an improved micro-electrode array and an improved method for producing such micro-electrode arrays.

The object is achieved by means of the micro-electrode array having the features of claim 1 and by means of the method having features of claim 11. Advantageous embodiments are described in the dependent claims.

For a micro-electrode array of the type mentioned in the introduction it is proposed that a plurality of measurement lines that are electrically insulated from one another are arranged around the core. Adjacent to the end surface of the core, at the end of the electrodes there are a plurality of electrode surfaces arranged in a manner distributed spatially around the end surface, said electrode surfaces in each case being electrically conductively connected to an associated measurement line. The associated measurement lines can be integrated in the same layer plane and/or in different layer planes in the micro-electrode array.

Consequently, a plurality of electrodes are arranged around the end surface. Neural activity can thus be measured spatially. This is advantageous in particular if the tissue situated in the direct vicinity of the electrode tip is damaged and the neural activity originates from more distant sites. With the plurality of electrodes per electrode tip it is thus possible to obtain a more differentiated signal, from which an evaluation of neural activity in the vicinity of the micro-electrode array is readily possible.

As a result of the provision of a plurality of measurement sites, it is necessary for same to be contacted by individual measurement lines embodied as strip lines that are as narrow as possible. This reduces the immense capacitance of previous concentric metallizations with respect to the surrounding tissue, which then allows the measurement of individual action potentials. It also becomes possible to separate the signals measured in a spatially distributed manner for the individual electrode openings, since they have scarcely any mutual influence among one another and toward the tissue.

The core with its high aspect ratio, i.e. length greater than thickness (diameter), provides a carrier for the electrodes and associated measurement lines. It can moreover be used as necessary in the form of a light guiding core having a light exit surface as end surface as waveguide for electromagnetic waves in the visible and/or non-visible wavelength range (e.g. infrared, ultraviolet, terahertz) in order to stimulate cells.

In contrast to the simple conventional coating of the lateral surface of a conically tapering electrode, what is achieved by the arrangement of a plurality of measurement lines at the lateral surface at the outer surface of the core is that the electrical behavior is improved.

For this purpose, the measurement lines can be arranged in a manner distributed around the circumference of the outer surface of the core. Moreover, a multilayer construction can allow the electromagnetic shielding of individual measurement lines from one another.

If instead of concentric or partly concentric electrically conductive layers for the purpose of forming measurement lines conductor tracks are patterned directly onto the lateral surface of the cores, the capacitance of the conductive surface toward the surrounding tissue decreases. Since the impedance of the electrode contacts is relatively high, the parasitic capacitances that occur in the case of the concentric coating of the lateral surface of the cores lead to a severe damping of high-frequency signals, in particular of the signals of the action potentials of the cells. This is avoided as a result of a plurality of measurement lines that are electrically insulated from one another being applied to the outer surface of the core. At the very least the parasitic capacitances are significantly reduced.

As an alternative to simple outgoing electrodes, field effect transistors can be used for detecting weak electrical signals or electrostatic potentials. In contrast to simple outgoing electrodes, said transistors require both a feed line and an outgoing line, but directly amplify the measured signal and can thus contribute to more sensitive detection with less noise. As a result of an applied voltage on these lines, the system open to the neuron environment between the contacts, as a result of a change in potential, can alter the conductivity and thus the current that flows. In this case, the open surface between the two contacts acts wholly or in large part as a gate electrode. Transistors on the basis of polar semiconductors are preferably used here, since the latter have a particularly high sensitivity. Field effect transistors on the basis of compound semiconductors from the group III nitrides, in particular GaN, are very well suited here. In this case, GaN has a high biocompatibility and long-term stability in living organisms. However, the properties of the gate region can also additionally be modified by coatings and the sensitivity can thus be influenced. In particular, it can be electrically insulated from the neuron environment very well by highly insulating layers such as silicon dioxide or silicon nitride, for example, in order to minimize a possible influence.

The core can be cylindrical and can have a base surface at its free end, on the plane of which the central end surface (e.g. the light exit surface of a light guiding core) and a plurality of electrode surfaces arranged in a manner distributed around the circumference of the central end surface are arranged. Cylindrical columnar cores are thus proposed instead of tapering conical electrodes. On account of the lateral surfaces of the light guiding cores, which lateral surfaces are free of undercuts but virtually perpendicular (95°±5°) to the plane of the substrate, said columnar cores can be adequately patterned for the purpose of forming measurement lines at the lateral surface. Moreover, such cylindrical columnar cores can be readily produced in the layer construction integrally in the flexible substrate, as a result of which an integral flexible micro-electrode array is provided which, upon being introduced into tissue, has a significantly reduced destructive influence on the tissue. Moreover, the base surface of the cylindrical light guiding core provides a surface region around the central end surface on which electrode surfaces can be applied. Said base surface can be planar, slightly curved or inclined. It is advantageous, however, if the base surface does not taper, in order to reduce the risk of destruction of tissue.

The flexible substrate is preferably polymer-containing. It can be formed from a polyimide, for example, such that a progressive implantation of individual electrodes is possible on account of the high flexibility. As a result, tissue damage can be reduced and the blood supply can be adversely affected to a lesser extent since the pressure that occurs during the implantation can be reduced. Moreover, light emitters, such as light emitting diodes, for example, and electrical lines can be incorporated easily and well into such a flexible polymer structure.

The core can be formed from a polymethyl acrylate (PMMA), which is also well suited as a light guide. Both the polymer-containing substrate and the PMMA columnar core can be lithographically patterned well in order to form electrode lines and electrode surfaces. The polymer-containing substrate can be integrally combined well with the PMMA columnar core if the columnar core is formed in a layered manner by applying PMMA material on the substrate. Furthermore, the columnar core can also be constructed from one piece in a plate-like manner, and be directly bonded and lithographically patterned. In all embodiments, the PMMA columnar core here is itself still so flexible that tissue damage is thereby reduced.

The core can be surface-treated. In this case, it is advantageous, by patterning the lateral surface of a light guiding core, to adapt for example the refractive index at the outer side of the light guiding core. Reducing the refractive index ("graded index") at the outer surface of the light guiding substrate improves the light guiding in the light guiding core (waveguide) without the need for a specularly reflective metallic coating at the outer side of the light guiding core, which hitherto has additionally been used as a measurement line. A coating of the light guiding core by a second transparent material having a lower refractive index (step index) than the light guiding core is also conceivable. The measurement lines thus no longer need be used as part of the optical system, but rather can be patterned exclusively with regard to their electrical function, e.g. in narrow tracks at the outer side of the light guiding core. The measurement of action potentials can thus be improved.

An improvement of the light emitter, in particular a smaller light excitation volume and thus a more targeted excitation of the neurons, can be achieved significantly better by the use of highly directional light sources by comparison with an emitter that emits into the entire half-space. As an extension of simple LEDs, so-called Resonant Cavity LEDs (RCLED), which usually have a dielectric or monolithic Bragg mirror, are suitable for this purpose. As a result, the emission from the surface of the LED is highly directional. A further improvement can be achieved by means of vertically emitting lasers (Vertical Cavity Surface Emitting Laser, VCSEL), in which a second Bragg mirror above the RCLED additionally leads to a highly directional coherent light emission with a small aperture angle, as a result of which, depending on the component diameter, it is possible to realize light beams in the near field with diameters of less than 10 μm and a small aperture angle. Thus, in principle, e.g. individual neurons or neuron populations can be addressed with high accuracy. One advantage of such light emitters, moreover, even though they are of small design, is that they nevertheless allow a high light power to be achieved in a small volume and, on the other hand, they consume only a low power, which leads to a simplification of the driving since, firstly, the lines are thin and, secondly, the power loss concomitantly introduced as heat is low.

In principle, a good focusing of the light can also be realized by means of a modified embodiment of the light guiding core. Here there are a number of possibilities for achieving this. Firstly, a curvature of the light exit or the embodiment of the cylinder end surface as a lens can lead to a collimation of the light beam. Given knowledge of the penetration depth and the approximate spacing of the neurons to be addressed, the focusing permits a targeted addressing of the neurons since the beam, given a short focal length, has a sufficient intensity for exciting a neuron or a group of neurons only in a small depth range or distance from the light exit opening.

Another possibility for improvement results from a patterning of the surface of the light guiding cylinder by introducing or applying thickness modulations or vapor-deposited materials such as metals or other dielectrics as light guides at regular intervals. This brings about, in a manner similar to a Bragg mirror, the reflection of a wavelength band which can be selected such that only a wavelength range of the light emitted by the LED has a high transmission through the waveguide, as a result of which the power radiated in total onto the neurons is reduced and, in the case of sources having a broader bandwidth, only the wavelength suitable for the excitation penetrates into the tissue. In principle, the optical waveguide can also be used wholly or partly as an upper mirror for a VCSEL. Thus, in this case, the light source consists of an RC-LED with mirror at the bottom, and the optical waveguide the by one of the above methods as upper mirror, now in resonance with the lower mirror and the cavity in which the light emitting layer is seated. By means of directional light sources, on account of the higher light intensity in the emission direction, the component size can be significantly reduced and the packing density of such individually addressable light sources on the carrier can be significantly increased as a result of which a more accurate addressing of individual neurons or small groups of neurons is possible and complex excitation patterns can be transmitted more easily.

The lateral surface of the core can be patterned lithographically for the purpose of forming the measurement line and electrode surfaces. Preferably, light emitters are carried by the substrate, said light emitters being arranged in each case in a manner adjoining the transition from a light guiding core to the substrate. As a result of the construction or incorporation of a light emitter, such as a light emitting diode, for example, in the transition between substrate and light guiding core, the light emitted by the light emitter is transmitted virtually without any losses via the light guiding core to the light exit surface at the free end of the respective electrode.

The cores of the micro-electrode array can be formed with different lengths in order to reach cortical regions at different depths. In this case, it is also conceivable for electrodes and/or light emitters to be present on the substrate surface (i.e. the height of the electrodes is zero). A planar measurement can thus be combined with a three-dimensional measurement of neural activity.

The production of the micro-electrode array is accomplished by a material being applied in a layered manner on a flexible substrate or being bonded as a plate-shaped material layer directly onto a flexible substrate in order to form columnar light guiding cores. These cores can be directly applied for example as light guiding cores on or in the substrate arranged light emitters (for example light emitting diodes) and combine integrally with the flexible substrate. This is followed by a step of laminating in the cores and/or directly forming a plurality of measurement lines at the lateral surface of the cores by means of lithographic patterning. This lithographic patterning can be performed directly on the material of the core or on a coating of the core or on a thin polymer structure layer (lamination layer), which then respectively forms the lateral surface. For the lithographic patterning, by way of example, a photosensitive resist can be applied on the lateral surface of the cores and, after exposure and removal of the regions exposed to a lesser or greater extent, can be filled with electrically conductive material by sputtering, vapor deposition or the like in order to form the plurality of measurement lines with reduced width by comparison with the circumference of the lateral surface, and also the electrode surfaces, if appropriate, in a lift-off process, for example.

A multilayered metallization of the substantially cylindrical columnar structures from above, i.e. from the opposite side relative to the substrate, is possible. This allows the use of standard processes on Si wafers, without the need for glass wafers for patterning the cores from below, i.e. through the substrate.

In this way, a monolithic micro-electrode array is provided in a simple manner, which micro-electrode array has a plurality of electrode surfaces adjacent to the end surface of the core, which electrode surfaces can be connected to a measuring unit or evaluation unit via respectively assigned measurement lines.

The micro-electrode array should be passivated with a polymer-containing material, such as e.g. polyimide, such that only the electrodes electrically contact neural tissue with their electrode surfaces.

Figure 2:
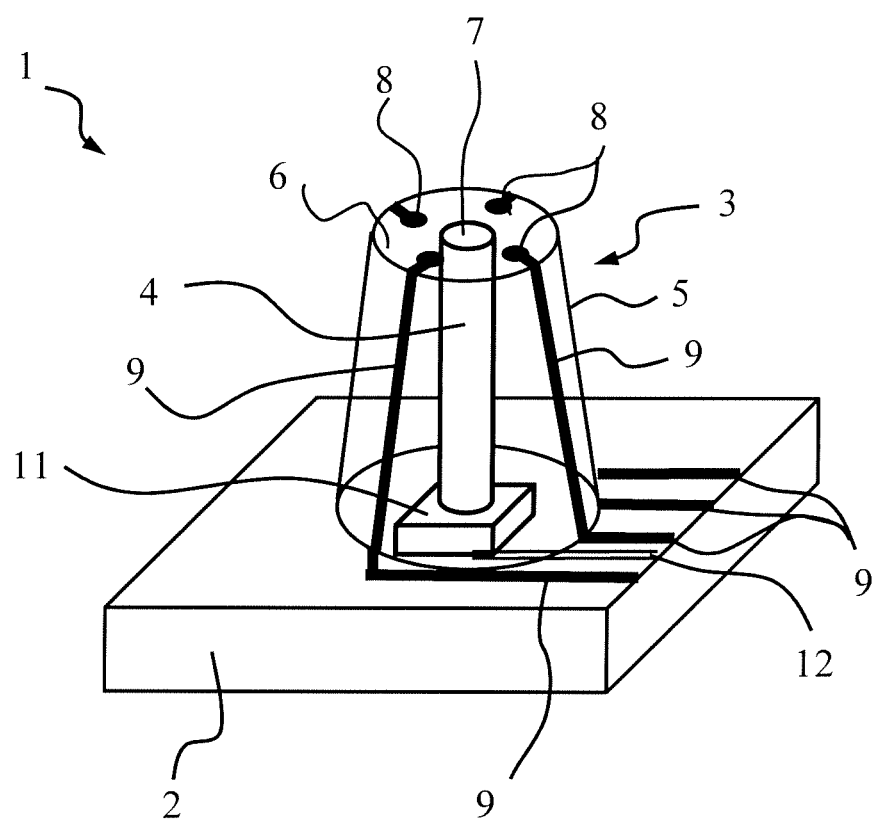
Figure 3:
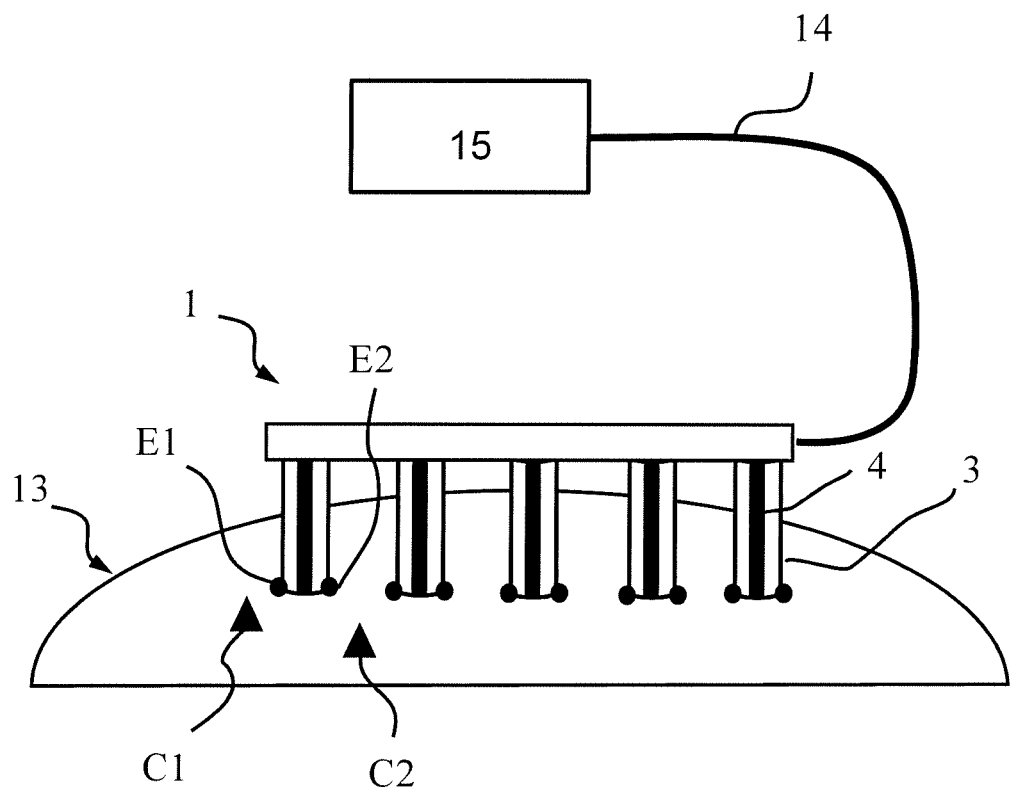

The invention is explained in greater detail below on the basis of an exemplary embodiment with the accompanying drawings, in which:

FIG. 1—shows a perspective schematic diagram of a micro-electrode array;

FIG. 2—shows an excerpt view of the micro-electrode array from FIG. 1 with an electrode arranged on a substrate;

FIG. 3—shows a schematic diagram of a micro-electrode array introduced into a tissue, which micro-electrode array is connected to an evaluation unit, with exemplary electrode signals with and without optical stimulation.

FIG. 1 reveals a perspective schematic diagram of a micro-electrode array 1 having a flexible substrate 2. The flexible substrate 2 is formed from a polymer, for example, and thus relatively soft and compliant during the implantation of the micro-electrode array 1 into tissue. By way of example, polyimide is suitable as a basic material for producing the substrate 2.

Light emitters can optionally be secured (not visible) in or on the substrate. Electrodes 3 are then built up in a layered manner on the substrate 2, optionally above a respective light emitter. The electrodes 3 are arranged in a matrix at a distance from one another in rows preferably at equal distances. The electrodes 3 have a core 4 applied monolithically or in a layered manner on the substrate 2, said core consisting of a different material than a layer structure 5 surrounding the core 4, for example PMMA or SUB. Said layer structure 5 together with the core 4 forms an electrode column which is approximately cylindrical and has a base surface 6. It is evident that the electrodes 3 do not taper at the base surface 6 and the electrode walls are virtually perpendicular to the plane of the underlying substrate 2. They can also be slightly inclined (in the range of approximately 0 to 5 degrees, without an undercut), but should not be conical. The core 4 can be formed from a light guiding material in order to serve as a waveguide for visible and/or non-visible light for the stimulation of cells.

A central end surface 7 of the core 4 is present at the base surface 6. Said end surface 7 forms a light exit surface for the e.g. light guiding cores 4. Furthermore, on the base surface 6 electrode surfaces 8 are arranged in a manner distributed circumferentially around the central end surface 7. Said electrode surfaces 8 are electrically conductively connected in each case to an assigned measurement line 9, which are led at the lateral surface of the electrodes to the substrate 2. In the substrate 2, the measurement lines 8 are then led to a connecting line 10, via which an evaluation unit can then be connected.

FIG. 2 reveals a schematic diagram of an excerpt from a micro-electrode array 1 from FIG. 1. It now becomes clear that the substrate 2 can carry a light emitter 11, e.g. a light emitting diode, which can optionally be driven via a control line 12 in order to emit light signals and thus optically stimulate tissue. The light emitted by the light emitter 11 is then emitted at the central end surface 7 (light exit surface) via the light guiding core 4. The neural activity that results after such an optical stimulation can then be measured with the aid of the electrode surfaces 8 arranged spatially around the end surface 7. Over and above the arrangement of electrode surfaces 8 on the base surface 6, even further electrode surfaces 8 can also be present at the circumference of the lateral surface of the electrode 3.

The layer structure 5 surrounding the core 4 is configured then such that measurement lines 9 are led at the lateral surface from the base surface 6 of the electrode 3 toward the structure 2. In this case, the measurement lines 9 are electrically insulated from one another and arranged in a manner distributed over the circumference. In a departure from the schematically depicted illustration, said measurement lines can also be incorporated into the core 4, or into an intermediate layer, which is then surrounded by an electrically insulating layer, which then forms the outer surface of the electrode 3.

It becomes clear that the measurement lines 9 are then led on the surface of the substrate 2 or in the substrate 2 e.g. parallel to the plane of the substrate 2 at a marginal edge of the substrate 2 in order to be able to be led there in combination into an evaluation unit. The measurement lines 9 can also be combined in a connector, onto which a measurement cable of an evaluation unit is then clamped. The core 4 can be formed from polymethyl acrylate PMMA, for example. The layer structure 5 surrounding the core 4 can in turn be formed from the flexible material of the substrate 2, such as polyimide, for example. However, a soft outer coating applied by microengineering, which can consist e.g. of parylene or polydimethylsiloxane (PDMS), is also conceivable. As a result, in conjunction with the intrinsic flexibility of the polymer structure of the substrate 2, the immune response can be reduced further.

The light guiding cores 4 have a higher refractive index (graded index) than the surrounding structure material 5. This can also be ensured by means of different materials or by means of surface processing of the lateral surface of the light guiding core 4. By reducing the refractive index of the light guiding core 4 at the outer column surface (lateral surface) thereof or by coating the lateral surface of the light guiding core 4 with a second transparent material having lower refractive index (step index), good light guiding with the lowest possible light losses is achieved. The light emitted by the light emitter 11 is then emitted to the greatest possible extent only at the central light exit surface 7.

As a result of the patterning of the measurement lines 9 as conductor tracks on the lateral surface of the electrode 3, the capacitance of the conductive surface with respect to the surrounding tissue is considerably reduced in comparison with the concentric or partly concentric configuration of measurement lines 9. On account of the high impedance of the electrode surfaces 8 (electrode contacts), high parasitic capacitances are disturbing primarily for high-frequency signals such as occur in the case of action potentials of the cells.

The provision of a plurality of electrophysiologically differentiating electrode surfaces 8 distributed around the end surface 7 allows the derivation or differentiation of deeper signal sources, i.e. of neural activity, with the aid of triangulation methods. This is important in particular if tissue situated directly around the electrodes 3 was damaged by the introduction of the micro-electrode array 1. The fact that the electrode surfaces 8 are punctiform or rectangular, and at any rate not concentric, results in a reduction of signal-degrading effects caused by parasitic capacitances that would arise on account of a concentric complete metallization. The reduction of the width of the measurement lines 9, i.e. of the feed lines, over the circumference of the columnar electrodes 3 further reduces the parasitic capacitances that are applied on this conductor track along the columnar electrodes 3, i.e. on different lateral surfaces of the electrode 3 having mutually different radii.

FIG. 3 reveals a schematic diagram of the micro-electrode array 1 from FIG. 1 in a state in which said micro-electrode array 1 is implanted into tissue 13, for example that of a brain. The micro-electrode array 1 has, at its electrodes 3, electrodes 8 distributed around the end surface 7 of the core 4, two electrodes E1, E2 of which are schematically depicted by way of example. It becomes clear that the micro-electrode array 1 is connected to an evaluation unit 15 via a measurement cable 14. The evaluation unit 15 can have suitable measurement amplifiers and is also configured for optionally driving the light emitters 11.

Neurons C1, C2 of the tissue 13 are schematically depicted by way of example.

By way of example, the signals of the nerve cells C1 and C2 as recorded by the electrodes E1 and E2 arise for a spontaneous activity. In this case, the black line is the activity of the nerve cell C1 that is closer to the electrode surface E1. The dashed line is the spontaneous activity of the nerve cell C2 that is closer to the second electrode surface E2.

It is evident that the electrode surface E1 records in activity of the closer nerve cell C2 with the higher amplitude and the activity of the more distant nerve cell C2 with a lower amplitude. The signal relationship is correspondingly reversed for the second electrode E2.

If the second nerve cell C2 is a cell made sensitive to light by an excitatory optogenetic opsin, then only this nerve cell C2 responds to light pulses from the light guiding core 4 (light on). The nerve cell C1 then shows no activity (solid black line for the activity of the nerve cell C1).

Spatial selectivity of the electrode surfaces E1, E2 lying close together, of which there should therefore always be at least two electrode surfaces 8 per electrode 3, results in a better possibility for separation of signals of different nerve cells.

The micro-electrode array 1 is produced by a method comprising the following steps:
a) applying material on a flexible substrate 2 for the purpose of forming columnar cores 4, and
b) lithographic patterning on the lateral surfaces of the columnar electrode 3 in order to form at the core 4 or a lateral surface surrounding the core 4 a plurality of measurement lines 9, which are electrically insulated from one another, and of electrode surfaces 8, which are connected respectively to an associated measurement line 9, wherein the electrode surfaces 9 are arranged in a manner distributed spatially around the end surface 7 of the core 4,
c) passivation of the overall structure formed with keeping open or opening of the electrode surfaces.

The passivation of the surface of the overall structure can be carried out e.g. by coating with a polymer, such as e.g. polyimide. In this case, the electrode surfaces 8, E1, E2 can be kept open by covering in order to provide a surface that is freely accessible toward the outer side. However, after the coating, it is also possible to carry out an e.g. lithographic-based opening of the electrodes 3 by means of a dry etching method, for example.

The lithographic patterning can be carried out using photoresists (e.g. SU8 and polyacrylic) as material for the core 4. However, it is also conceivable to carry out production by means of printing or molding methods for building up the columnar electrodes 3 and in particular the cores 4, if possible also a 3D rapid prototype process for forming the columnar electrodes 3 in a layered manner. By virtue of the core 4, the brain tissue can be penetrated orthogonally to the surface of the micro-electrode array 1 and it is not necessary to fold over parts of the micro-electrode array 1. The micro-electrode arrays 1 are produced monolithically in such a microfabrication process.

The electrodes 3 themselves can be realized as openings on the base surface 6 or the lateral surface of the electrodes 3 to which an electrically conductive electrode surface 8 is adjacent.

In the case of a micro-electrode array 1, it is also conceivable for individual electrodes 3 not to be configured for optical stimulation, but to have a stabilizing core comparable to the light guiding core 4.

The cores 4 can be formed with different lengths in order to reach cortical regions of different depths.

The invention claimed is:

1. A micro-electrode array, comprising:
a flexible substrate;
a multiplicity of electrodes for electrically measuring neural activities, wherein the electrodes are arranged on the substrate, project from a plane of the substrate, and each of the electrodes has a light guiding core configured to transmit light to a light exit surface at a free end of the respective electrode, wherein the light guiding core is integrally connected to the flexible substrate and is flexible;
a plurality of measurement lines that are electrically insulated from one another arranged distributed around a circumference of the light guiding core of each electrode and extend from the flexible substrate to a base surface at the free end of the respective electrode; and
a plurality of electrode surfaces each of which is located on the base surface adjacent to an end surface of the light guiding core at the free end of each electrode, wherein the plurality of electrode surfaces are distributed spatially around the end surface of each light guiding core of each electrode, wherein each of the electrode surfaces is electrically conductive and is connected to an associated measurement line,
wherein the base surface at the free end of each electrode forms the light exit surface of the respective light guiding core.

2. The micro-electrode array as claimed in claim 1 wherein each light guiding core is cylindrical and wherein the plurality of electrode surfaces are distributed around a circumference of the end surface of the light guiding core.

3. The micro-electrode array as claimed in claim 1 wherein the substrate comprises a polymer.

4. The micro-electrode array as claimed in claim 1 wherein the light guiding core is formed from polymethyl methacrylate.

5. The micro-electrode array as claimed in claim 1 further comprising a surface treatment on the end surface of the light guiding core.

6. The micro-electrode array as claimed in claim 1 wherein either or both the light guiding core or a layer structure surrounding the light guiding core is lithographically patterned to form the measurement lines and electrode surfaces.

7. The micro-electrode array as claimed in claim 1 wherein the light exit surface has a curvature.

8. The micro-electrode array as claimed in claim 1 wherein a refractive index of a lateral surface of the light guiding core is greater than a refractive index of a layer surrounding the light guiding core.

9. The micro-electrode array as claimed in claim 1 further comprising a plurality of light emitters carried by the substrate, the plurality of light emitters being arranged in each case in a manner adjoining a transition from a light guiding core to the substrate, the light emitter being one of the plurality of light emitters.

10. The micro-electrode array as claimed in claim 1 wherein the multiplicity of electrodes have mutually different lengths.

11. The micro-electrode array as claimed in claim 9 wherein one or more of the plurality of light emitters are configured as a light emitting diode with a mirror that reflects emitted light.

12. The micro-electrode array as claimed in claim 9 wherein one or more of the plurality of light emitters are configured as a surface emitting laser.

13. The micro-electrode array as claimed in claim 1 wherein the electrodes comprise field effect transistors.

14. The micro-electrode array as claimed in claim 13 wherein the field effect transistors are composed of a polar material, wherein the field effect transistors have a source contact, a drain contact and a gate contact, and wherein a surface situated between the source contact and drain contact is configured wholly or partly as a gate contact, wherein the gate contact is in contact with an environment to be measured.

* * * * *